United States Patent [19]

Tsubota et al.

[11] Patent Number: 5,049,417
[45] Date of Patent: Sep. 17, 1991

[54] METHOD FOR PRODUCING AN AIR-PERMEABLE ADHESIVE TAPE

[75] Inventors: Kenji Tsubota, Ikeda; Nobuo Hanatani, Takatsuki, both of Japan

[73] Assignee: Sekisui Kagaku Kogyo Kabushiki Kaisha, Osaka, Japan

[21] Appl. No.: 565,789

[22] Filed: Aug. 13, 1990

[30] Foreign Application Priority Data

Jan. 16, 1990 [JP] Japan .................................... 7757
Jan. 16, 1990 [JP] Japan .................................... 7759
Apr. 27, 1990 [JP] Japan................................ 113046

[51] Int. Cl.$^5$ ............................................. B05D 5/10
[52] U.S. Cl. .................................. 427/208.6; 156/230; 427/208.8; 427/373; 427/385.5
[58] Field of Search ................... 427/208.6, 208.8, 373, 427/385.5; 156/230

*Primary Examiner*—Bernard Pianalto
*Attorney, Agent, or Firm*—Armstrong, Nikaido, Marmelstein, Kubovcik & Murray

[57] ABSTRACT

A method for producing an air-permeable adhesive tape comprising a substrate and a porous adhesive layer formed on said substrate is provided. The method comprises the steps of: forming a layer of a solution on a substrate, said solution containing an adhesive material in an organic solvent; applying water drops on said layer of said solution while said organic solvent remains in said layer, thereby allowing water drops to sink into said layer, the diameter of said water drops being in the range of 10 to 1000 μm, and the total amount of said water drops applied onto the surface of said layer being 5 to 200 g/m$^2$; evaporating said organic solvent contained in said layer of the solution, thereby forming an adhesive layer that contains said water drops; and evaporating said water from said adhesive layer, thereby forming communicating pores extending from the external surface to the inner surface of said adhesive layer.

8 Claims, 2 Drawing Sheets

1

METHOD FOR PRODUCING AN AIR-PERMEABLE ADHESIVE TAPE

BACKGROUND OF THE INVENTION

1. Field of the invention

The present invention relates to a method for the production of an air-permeable adhesive tape for medical and other applications. This type of adhesive tape also includes preparations in sheet form.

2. Description of the prior art

Adhesive plaster and other types of adhesive products employed in the medical field are directly applied to the surface of the body. The long continued application of such adhesive products to the human body prevents the dissipation of moisture from the surface of the skin, and may thereby cause skin inflammation. Therefore, adhesive products which are permeable to air are desirable, and accordingly the following techniques have previously been proposed for the purpose of manufacturing air-permeable adhesive materials.

(1) Japanese Patent Publication No. 51-8653

A gas or liquid incompatible with an adhesive material being used is dispersed in the form of minute bubbles or drops within a solution containing the adhesive material. The adhesive solution so obtained (hereinafter, "adhesive solution" is referred to as a solution containing an adhesive material) is then coated onto release paper, forming a layer of the adhesive solution. Next, this layer of adhesive solution is heated, thereby forming an adhesive layer and also bursting the gas bubbles or liquid drops so as to form communicating pores.

(2) Japanese Patent Publication No. 58-13116

A solution of an adhesive material in an organic solvent which can be extracted with an aqueous extractant is coated onto a porous backing, forming a layer of adhesive solution. This backing with the layer of adhesive solution is then immersed in the extractant, thereby extracting the organic solvent into the said extractant, and at the same time coagulating the said layer of adhesive solution. The replacement of the organic solvent by the extractant results in the formation of numerous communicating pores in the adhesive layer.

(3) Japanese Patent Publication No. 63-41585

An adhesive solution is prepared by uniformly dispersing water or a mixture of water and a water-absorptive macromolecular substance in an adhesive solution containing a pressure sensitive adhesive material and an organic solvent. This adhesive solution is coated onto the surface of a sheet with adequate surface releasing properties, thus forming a layer of adhesive solution, which is then dried, and an air-permeable backing is then layered on this adhesive layer.

In this process, when the layer of adhesive solution containing the dispersed water is dried, the organic solvent is first evaporated to form an adhesive layer, and then the water is evaporated, thus forming pores where water was present.

However, the existing methods described above possess the following shortcomings.

(1) With respect to Japanese Patent Publication Nos. 51-8653 and 63-41585:

In the processes comprising these existing techniques, an adhesive solution containing a uniformly dispersed gas or liquid incompatible with the adhesive material is used. However, a porous air-permeable tape with uniformly dispersed communicating pores cannot be obtained unless the uniform state of dispersion of the gas bubbles or liquid drops within the adhesive solution is adequately maintained.

Consequently, these processes entail difficult problems with respect to the preparation of the adhesive solution and control of the state of dispersion of the gas bubbles or liquid drops.

(2) With respect to Japanese Patent Publication No. 51-8653:

The previously existing technique described above suffers from the disadvantage that if, for example, the adhesive solution is coated onto the release sheet with a roll coater, then the water dispersed within the adhesive solution oozes from the layer of the solution by the pressure of the roller. Therefore, the method used for coating the adhesive solution onto the substrate is restricted.

Furthermore, since the water is dispersed within the adhesive solution in the form of drops with an extremely small diameter, when the layer of the adhesive solution is dried, the water is prone to evaporate together with the solvent. Consequently the formation of the desired communicating pores in the adhesive layer is difficult.

(3) With respect to Japanese Patent Publication No. 58-13116:

According to this previously existing technique, the use of the aforesaid adhesive solution is unnecessary. However, this technique does not permit the preparation of a tape with desirable air permeability.

SUMMARY OF THE INVENTION

The method for producing an air-permeable adhesive tape of this invention, which overcomes the above-discussed and numerous other disadvantages and deficiencies of the prior art, comprises the steps of: forming a layer of a solution on a substrate, said solution containing an adhesive material in an organic solvent; applying water drops on said layer of said solution while said organic solvent remains in said layer, thereby allowing water drops to sink into said layer, the diameter of said water drops being in the range of 10 to 1000 μm, and the total amount of said water drops applied onto the surface of said layer being 5 to 200 g/m$^2$; evaporating said organic solvent contained in said layer of the solution, thereby forming an adhesive layer that contains said water drops; and evaporating said water from said adhesive layer, thereby forming communicating pores extending from the external surface to the inner surface of said adhesive layer.

In a preferred embodiment, the substrate is an air-permeable sheet.

In another preferred embodiment, the substrate is a sheet with releasing properties, and the said method further comprises the steps of, layering an air-permeable sheet on the surface of said adhesive layer with communicating pores, thereby transferring said adhesive layer onto said air-permeable sheet.

In a preferred embodiment, the adhesive material is a rubber-base or synthetic resin-base adhesive material.

In a preferred embodiment, the synthetic resin-base adhesive material comprises an acrylic adhesive which is a copolymer obtained from a macromer.

In a preferred embodiment, the macromer is a monomer of number average molecular weight 1,000 to 20,000 containing at least one vinyl group, and the said monomer is at least one selected from the group consisting of polystyrene, polymethyl methacrylate, and polystyrene-acrylonitrile monomers.

In a preferred embodiment, the interfacial tension between said organic solvent and water is 20 dyn/cm$^2$ or more at 20° C.

In a preferred embodiment, the water applied on the layer of the solution contains a crosslinking agent capable of crosslinking the adhesive material.

Thus, the invention described herein makes possible the objectives of:

(1) providing a method for producing an adhesive tape with adequate air permeability;
(2) providing a method for producing an air-permeable adhesive tape, in which any restriction upon the means used for application of the adhesive solution onto the backing is not necessary; and
(3) providing a simple method for producing an air-permeable adhesive tape on an industrial scale.

BRIEF DESCRIPTION OF THE DRAWINGS

This invention may be better understood and its numerous objects and advantages will become apparent to those skilled in the art by reference to the accompanying drawings as follows.

DESCRIPTION OF THE PREFERRED EMBODIMENTS

Figure 1A:
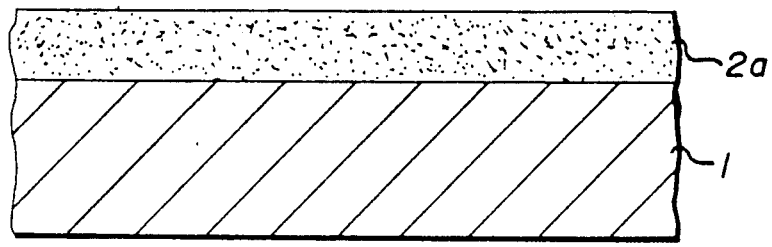
FIGS. 1A to 1C are process diagrams illustrating the method of the production of an air-permeable adhesive tape of the present invention.

As shown in FIG. 1A, an adhesive solution is coated on a substrate I, thereby forming a layer of adhesive solution 2a. As described below, the subadhesive strate is an air-permeable sheet or a sheet with releasing properties.

Any of various well-known methods may be employed for the coating of the said adhesive solution onto the substrate, for example, a roller coater, a knife coater, an extrusion lip, etc. can be used.

The aforesaid adhesive solution is prepared with an appropriate viscosity. The viscosity of the adhesive solution should desirably be in the range of about several thousands up to about 10,000 cps. The amount of the adhesive solution to be coated on the surface of the substrate will vary according to factors such as the type of adhesive material and organic solvent to be used, but ordinarily should be in the range of 20-250 g/m$^2$, and more preferably, of the order of 150 g/m$^2$. The thickness of the adhesive layer 2b (in dried state; see FIG. 1C) should desirably be 5-100 100 $\mu$m, and preferably, 10-80 $\mu$m, in the dry state.

Figure 1B:
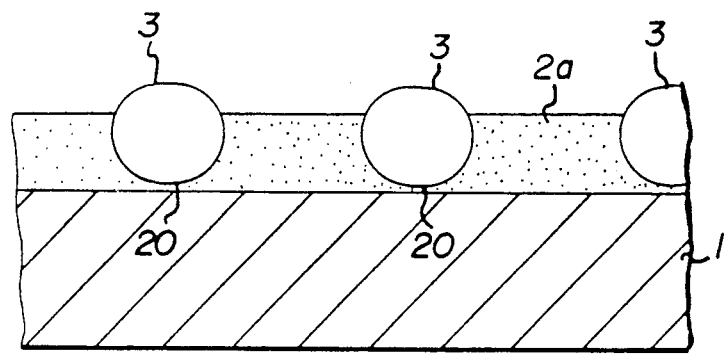

Next, shown in FIG. 1B, while the layer 2a of adhesive solution is still in the undried state (i.e., while the organic solvent remains in the layer), water drops are applied onto the surface of the layer 2a, thereby allowing water drops to sink into the layer 2a by their own weight. Generally, the water drops 3 extends from the external surface to the region very close to the inner surface of the layer 2a of the adhesive solution. The water drops do not completely come into contact with the substrate. A thin layer 20 of the adhesive solution exists between the water drop 3 and the substrate 1. The thin layer portion will crack when the layer of the adhesive solution is dried, thus obtaining air permeability as described below.

The water drops can be applied sprayed with any conventional spraying device such as a spray gun, etc. The diameters of the water drops should be in the range of 10-1000 $\mu$m. Preferably, the diameter is larger than the width of the layer of the adhesive solution. If the diameters of the water drops are less than 10 $\mu$m, then, after drying the layer of the solution, the formation of communicating pores in the resulting adhesive layer is difficult. Moreover, even assuming that communicating pores are formed in the adhesive layer, the diameters of these communicating pores are unduly small, consequently, when the adhesive layer possessing the said pores comes into contact with another sheet or with the surface of the skin, the pores may be obstructed. On the other hand, if the diameters of the water drops exceed 1000 $\mu$m, then the said water drops are not imbedded within the layer of adhesive solution, and therefore the desired communicating pores cannot be formed.

The amount of water applied onto the layer of adhesive solution 2a should be in the range of 5-200 g/m$^2$. If the applied amount is less then 5 g/m then the number of communicating pores formed will be inadequate. Whereas if the amount exceeds 200 g/m$^2$, then the drying of the applied water drops requires considerable time. Moreover, the drying process requires a greater amount of energy, which raises production costs. Furthermore, water that had been applied on the layer spreads over the surface of the layer, thus the desired communicating pores cannot be formed.

Figure 1C:
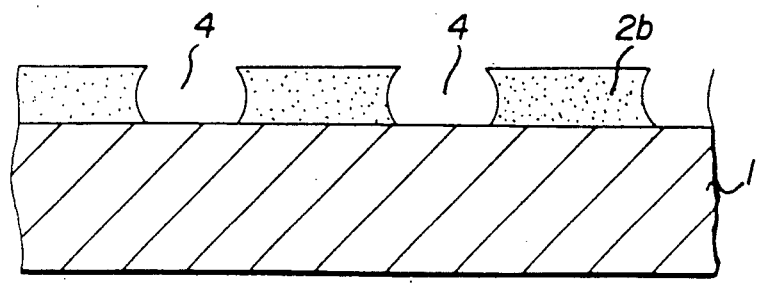

Next, as shown in FIG. 1C, the layer of adhesive solution 2a is dried, thereby forming an adhesive layer 2. In this drying process, the organic solvent and water contained in the layer of the adhesive solution 2a are evaporated. The evaporation of water is somewhat slower than the evaporation of the organic solvent. Therefore, the layer of adhesive solution 2a is dried in a state such that residual water drops 3 are present, and finally communicating pores 4 are formed in the adhesive layer 2b at the sites of the residual water drops 3. In the abovementioned process, the thin layer 20 existing between the water drop 3 and the substrate 1 becomes contracted as the evaporation of the organic solvent proceeds, resulting in a cracking of the thin layer, thus, a communicating pore is formed.

The appropriate drying temperature will vary according to factors such as the type of organic solvent used, the amount of adhesive solution in the layer, and the amount of water applied on the layer, but in general, a temperature in the range of 70°-120° C. is desirable. Ordinarily, drying is performed by maintaining the layer at a temperature of approximately 110° C. for several minutes.

The adhesive solution used in the present invention is prepared by dissolving an adhesive material in an organic solvent. The said adhesive material can be either a rubber base adhesive material or a synthetic resin base adhesive material.

As the rubber base adhesive materials, a rubber base composition is used, which contains a rubber such as natural or synthetic rubber, a tackifier such as a rosin, terpene, or petroleum resin a softening agent such as an oil, and an organic solvent.

Applicable synthetic resin base adhesive materials include, for example, acrylic type polymers containing carboxylic acids which are obtained from vinyl type monomers containing carboxyl groups such as acrylic acid, methacrylic acid, etc.; acrylic type polymers containing hydroxyl groups which are obtained from vinyl type monomers containing hydroxyl groups such as 2-hydroxyethyl methacrylate, etc.; polyvinyl ether type polymers; and polyisobutyl type polymers. Acrylic adhesive materials are particularly suitable for the present purpose.

A suitable acrylic adhesive material is, for example, obtained from the copolymerization of an alkyl acrylate such as butyl acrylate, 2-ethylhexyl acrylate, or isononyl acrylate; a polar monomer such as acrylic acid, acrylamide, or N-vinyl-2-pyrrolidone, and other monomer such as an acrylate other than the acrylate mentioned above, methacrylate, styrene, vinyl acetate, etc.

The organic solvents applicable for use in the present invention include, for example, ethyl acetate, toluene, cyclohexane, n-hexane, and alkanes with 5 to 7 carbon atoms.

Organic solvent such that the interfacial tension between the said solvent and water at 20° C. is at least 20 dyn/cm are particularly desirable for the present purpose. Organic solvents satisfying this condition include, for example, toluene, cyclohexane, n-hexane, n-heptane, benzene, iodobenzene, hexadecane, nonylbenzene, nonane, carbon disulfide, dodecane, carbon tetrachloride, o-, m- or p-xylene, octane and ethylbenzene. Moreover, the organic solvent used need not necessarily be one of the above-mentioned substances, but can also be any suitable mixture of two or more organic solvents. For example, a mixed solvent consisting of ethyl acetate, having a interfacial tension with water of 6.8 dyn/cm, and cyclohexane, having an interfacial tension with water of 50.59 dyn/cm, can be used. The mixing ratio of ethyl acetate and cyclohexane should be such that the interfacial tension between the mixture and water be at least 20 dyn/cm.

The reason for requiring the interfacial tension between the organic solvent and water be at least 20 dyn/cm is as follows. If this condition is satisfied, then the water drops applied onto the surface of the layer of adhesive solution more readily assume a spherical form upon entering the said layer in the direction of thickness, thus, each water drop extends from the external surface to the region very close to the inner surface of the said layer. If the interfacial tension between water and the organic solvent is less than 20 dyn/cm, then the said organic solvent will display an excessive affinity with water, and consequently the water drops will tend to spread along the directions parallel to the surface of the adhesive layer. Thus, the formation of the desirable communicating structures will be difficult in the resulting adhesive tape.

The communicating pores in the adhesive layer can be formed more efficiently if an acrylic adhesive obtained by copolymerization of macromers is employed as the aforesaid adhesive material. The reasons for this are as follows.

As mentioned above, when the method of the present invention is employed in which communicating pores are formed by applying water drops onto the surface of a layer of adhesive solution containing an organic solvent, then not only the organic solvent but also the water must be removed by drying. Thus, a high temperature is necessary for the drying process.

In some cases, where the adhesive layer is formed with an adhesive solution containing a synthetic resin based adhesive material, the form of the adhesive layer is maintained by crosslinking the adhesive material during the drying process. However, the crosslinking of the adhesive material during the drying process is generally not complete, therefore if the drying temperature is high, the adhesive layer will melt and flow. As a result, the flow of the adhesive layer may obstruct the communicating pores.

On the other hand, if an adhesive solution containing an acrylic based adhesive material obtained by copolymerization of macromers is used, the adhesive layer formed by this adhesive solution will not flow, even if heated to a comparatively high temperature, and the communicating pores will not be obstructed.

The macromers applicable for use in the present invention should possess at least one vinyl group and have a molecular weight in the range of 1,000 to 20,000.

The macromers having these properties include polystyrene macromers, polymethyl methacrylate macromers, and polystyrene-acrylonitrile macromers. Macromers containing methacryloyl groups at a terminal of the molecule are particularly suitable for the present purpose. For example, the macromer includes the products manufactured by the TOA GOSEI CHEMICAL INDUSTRY CO., LTD., and sold under the Trade names AS-6 (i.e., a polystyrene macromer), AA-6 (i.e., a polymethyl methacrylate macromer), AN-6 (i.e., a polystyrene-acrylonitrile macromer), etc.

Any of the various solvents mentioned, above can be used as an organic solvent for the purpose of dissolving the acrylic type adhesive obtained by the copolymerization of the aforesaid macromer.

A crosslinking agent capable of crosslinking adhesive materials can be added to the water applied onto the adhesive layer.

If the water contains a crosslinking agent, then the portions of the layer of adhesive solution contiguous with the water drops undergo crosslinking, which facilitates the subsequent maintenance of the structural form of the water drops. Therefore, the shapes of the communicating pores formed in the resulting adhesive layer can be stably maintained, which can prevent the obstruction of the said communicating pores by deformation or flow of the adhesive layer.

If this crosslinking agent were contained in the adhesive solution itself, then the entire adhesive layer so formed would undergo crosslinking, and consequently the adhesiveness of the layer would be poor. However, if the aforesaid procedure is employed, then the adhesiveness of the adhesive layer material does not decrease.

The crosslinking agents applicable for the aforesaid purpose include the following compounds.

Examples of crosslinking agents for crosslinking an acrylic adhesive in which vinylcarboxylic acids such as acrylic acid and methacrylic acid are contained as monomer components include dimethylolphenolformaldehyde resin, trimethylolmelamine, and diamines or polyamines. The following compounds (1) to (12) can be used as the diamine or polyamine.

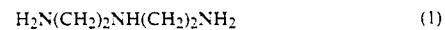

(1)

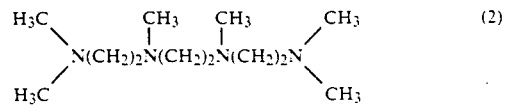

(2)

-continued

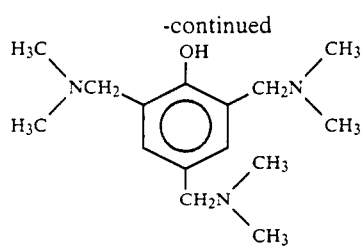 (3)

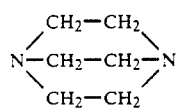 (4)

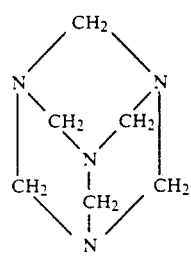 (5)

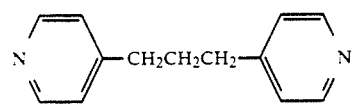 (6)

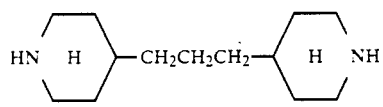 (7)

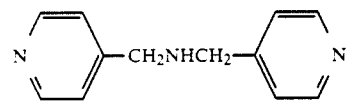 (8)

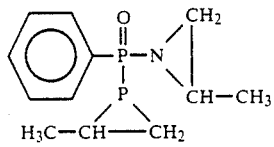 (9)

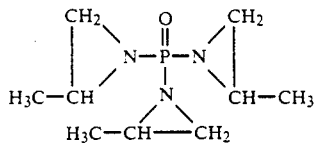 (10)

-continued

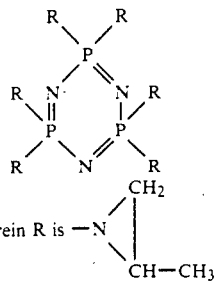 (11)

Wherein R is

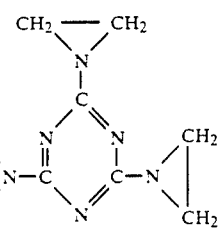 (12)

In addition to the above-mentioned compounds, the following isocyanate compounds can also be used as the crosslinking agent for acrylic adhesives.
(1) Paraphenylenediisocyanate
(2) 2-Chloro-1,4-phenyldiisocyanate
(3) 2,4-Toluene diisocyanate
(4) 2,6-Toluene diisocyanate
(5) 1,5-Naphthalene diisocyanate
(6) Hexamethylene diisocyanate
(7) COLONATE L (manufactured by Nippon polyurethane industry Co.,Ltd.)
(8) COLONATE HL (manufactured by Nippon polyurethane industry Co.,Ltd.)
(9) Millionate (manufactured by Nippon polyurethane industry Co.,Ltd.)
(10) COLONATE EH (manufactured by Nippon polyurethane industry Co.,Ltd.)
(11) Diphenylmethane-4,4'-diisocyanate
(12) 3,3'-Dimethyl-4,4'-biphenylene diisocyanate The following epoxy compounds can also be used as the crosslinking agent for acrylic adhesives together with a catalyst such as tertiary amine and quaternary ammonium salt. Furthermore, metal oxides and metal peroxides such as zinc oxide and zinc peroxide can also be used.

Halogenated bisphenol type: (1)

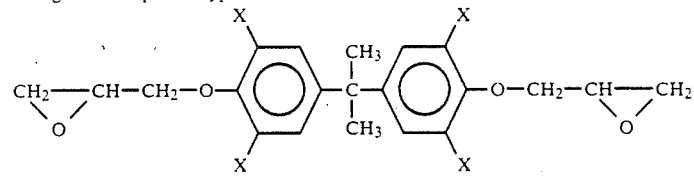

Wherein X is Cl or Br.

Resorcinol type: (2)

-continued
Bisphenol F type: (3)
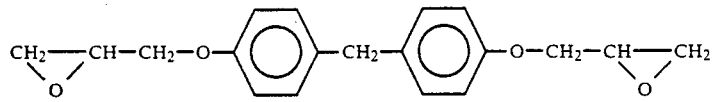
Tetrahydroxyphenylmethane type: (4)
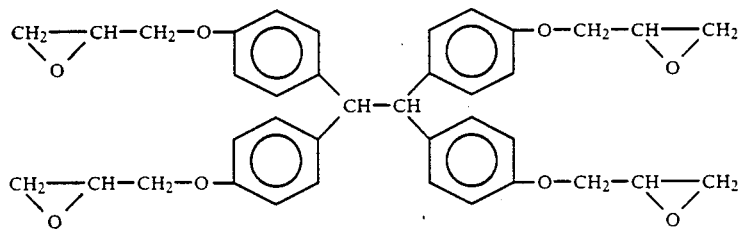
Novolak-type epoxy resin: (5)
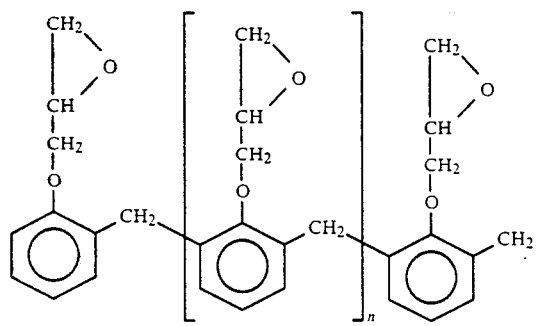
(6)
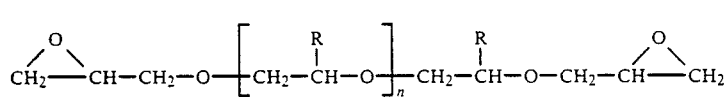
Glycerol triether type: (7)
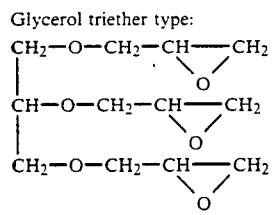
Polyolefin type epoxy resin: (8)
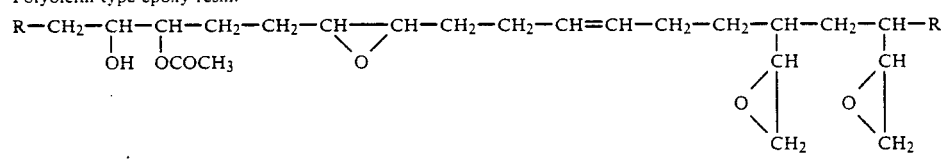
Soybean oil containing epoxy groups: (9)
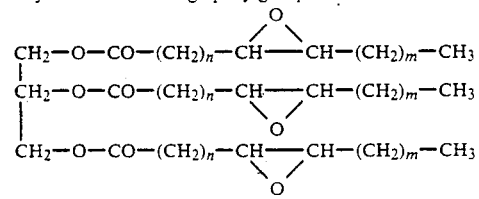
Vinylcyclohexene dioxide: (10)
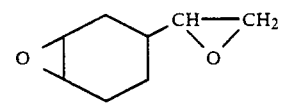
Dicyclopentadiene dioxide: (11)

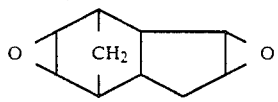

3,4-Epoxy-6-methylcyclohexylmethyl-3,4-epoxy-6-methylcyclohexanecarbonate: (12)

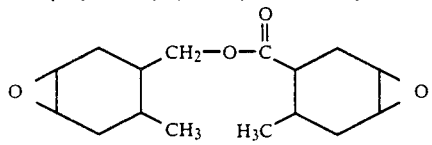

Dicyclopentadienyl metal dihalide represented by the formula MeCp$_2$Cl$_2$ can also be used as the cross-linking agent for acrylic adhesives, wherein Me is a metal selected from the group consisting of Ti, Zr and Hf; and Cp is cyclopentadiene. Organic metal compounds such as chromium trifluoroacetate can also be used as the crosslinking agent.

For the adhesive having hydroxy groups such as 2-hydroxyethyl methacrylate, the following compounds are useful as crosslinking agents: amino resin; halogen compounds represented by the formula RCl$_2$PO, wherein R is selected from the group consisting of C$_6$H$_5$-, Cl-CH$_2$-, C$_6$H$_5$O-, C$_2$H$_5$-, and the like; urea; the as tetrahydrofurantetracarboxylic anhydride, pyromellitic dianhydride, and benzophenonetetracarboxylic anhydride; dialdehydes such as glyoxal and terephthalaldehyde; the above-mentioned epoxy compounds; boric acid; phosphites; and alkoxides of Ti, Zr, and Al.

The substrate used in the present invention is an air-permeable sheet or a sheet with releasing properties.

Materials appropriate for use as the aforesaid air-permeable sheet include, for example, woven fabric, unwoven fabric, paper, foam sheets with open cells, or non-permeable material (e.g., synthetic resin sheets) with numerous minute performations. If the sheet used is composed of a material with a relatively large mesh, such as woven fabric, so that the adhesive solution is prone to leak through the sheet, then a filler such as rubber latex may be coated onto the porous sheet to prevent leakage.

As the aforesaid sheet with releasing properties, any material which possesses adequate releasing properties to the adhesive layer can be used. Representative types of the release sheets appropriate for the present purpose are silicone-treated releasing papers or releasing films. Other types of the release sheets include, for example, steel belts or rotating drums composed of metals such as stainless steel.

Figure 2:
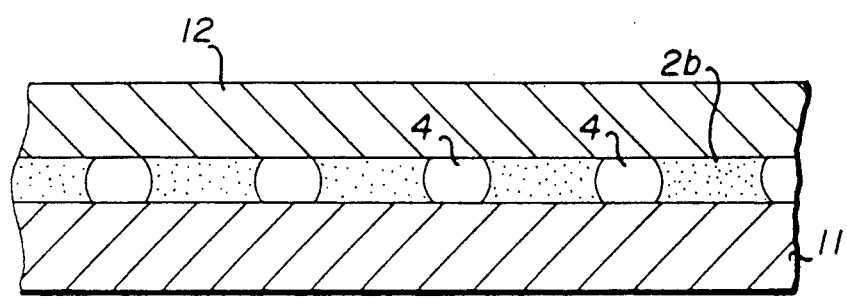
FIG. 2 is a cross-sectional view showing an example of the air-permeable adhesive tape obtained by the method of the present invention.

When the air-permeable sheet is used as the substrate, an air-permeable adhesive tape is obtained by the formation of a porous adhesive layer on the said substrate according to the method of the present invention. When a sheet with releasing properties is used as the substrate, then, after the adhesive layer has been formed on the surface of the substrate, an air-permeable sheet is layered on the surface of the adhesive layer, thereby, the adhesive layer is transferred to the air-permeable sheet, resulting in an air-permeable adhesive tape. This type of adhesive tape shown in FIG. 2, is composed of a release sheet 11, an adhesive layer 2b, and an air-permeable sheet 12. When the tape is to be used, the release sheet 11 is peeled away from the surface of the adhesive layer 2b.

Figure 3:
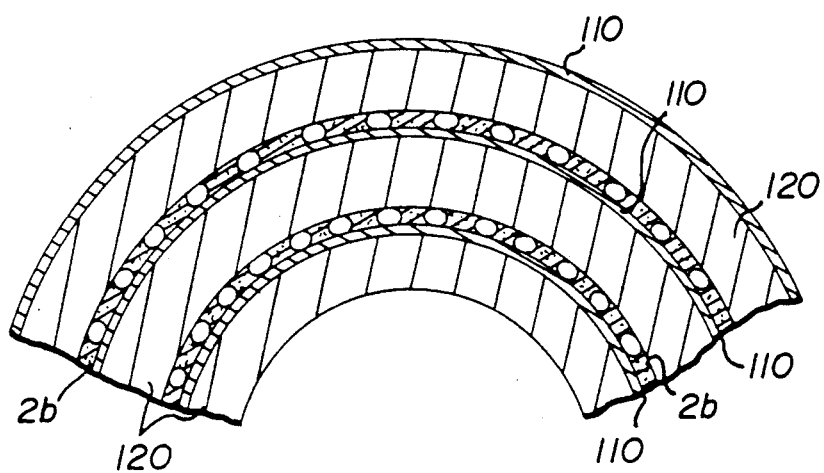
FIG. 3 is a cross-sectional view showing another example of the air-permeable adhesive tape obtained by the method of the present invention.

If an air-permeable sheet 120 having a releasing layer 110 on one side is used as a substrate, then an air-permeable adhesive layer 2b can be formed on a side other than the side of the releasing surface, and the resulting adhesive tape can be wound into a roll, as shown in FIG. 3. The form of the air-permeable tape is not limited to those mentioned above.

Examples

The physical properties of the air-permeable adhesive tapes prepared in the examples and comparative examples described below were evaluated in the following manner.

(1) The diameters and numbers of communicating pores formed in the adhesive layer were determined by inspecting the surface of the adhesive layer of the adhesive tape with a scanning electron microscope.

(2) Air permeability (i.e., the time required for 300 ml of air to pass through an air-permeable adhesive tape with an area of 6.45 cm$^2$) was determined using Gurley's Densometer (YASUDA SEIKI SEISAKUSHO, LTD.).

Unwoven polyester fabric (manufactured by the Dupont Corporation) was used as the substrate (i.e., air-permeable sheet) in the examples and comparative examples described below.

EXAMPLE 1

An adhesive solution was prepared by dissolving, in 700 parts by weight of n-hexane, an adhesive composition consisting of 100 parts by weight of natural rubber (SMR5L, produced in Malaysia), 50 parts by weight of zinc oxide, 75 parts by weight of hydrogenated rosin glycerin ester (Fioral 85; manufactured by the HERCULES INCORPORATED), 5 parts by weight lanolin, and 2 parts by weight of phenyl-$\beta$-naphthylamine (i.e., an antioxidant).

Next, this adhesive solution was coated onto release paper in the proportion of 200 g/m$^2$, and while the adhesive solution was still undried, water drops with diameters 300-500 $\mu$m were sprayed onto the surface of the adhesive solution in the proportion of 150 g/m$^2$, of the adhesive solution in the proportion of 150 g/m$^2$, after which the specimen was dried.

Next, an air-permeable sheet was layered on the adhesive layer so obtained in order to transfer the said adhesive layer to the air-permeable sheet, thereby obtaining an air-permeable adhesive tape.

COMPARATIVE EXAMPLE 1

The adhesive solution obtained in the process of Example 1 was coated onto release paper in the proportion of 200 g/m$^2$, then, while layer of the adhesive solution was still undried, water drops with diameters of 300-500 μm were sprayed onto the surface of the layer of the adhesive solution in the proportion of 3 g/m², after which the specimen was dried.

Next, an air-permeable sheet used in Example 1 was layered on the adhesive layer in order to transfer the said adhesive layer to the air-permeable sheet, thereby obtaining an air-permeable adhesive tape.

EXAMPLE 2

An adhesive solution was obtained by dissolving, in 750 parts by weight of toluene, an adhesive composition comprising 100 parts by weight of synthetic rubber (Quintack, manufactured by NIPPON ZEON CO., LTD.), 100 parts by weight of hydrogenated rosin ester (Estergum H, manufactured by ARAKAWA CHEMICAL INDUSTRIES, LTD.), 20 parts by weight of process oil, 5 parts by weight of mercaptobenzimidazole as an antioxidant.

Next, this adhesive solution was coated onto 1 an air-permeable sheet used in Example 1 in the proportion of 200 g/m², and while the layer of said adhesive solution was still undried, water drops with diameters of 500-800 μm were sprayed onto the surface of the layer in the proportion of 25 g/m², after which the specimen was dried, thereby obtaining an air-permeable adhesive tape.

EXAMPLE 3

The adhesive solution obtained in the process of Example 2 was coated onto an air-permeable sheet in the proportion of 200 g/m² in the same manner as in Example 2. Then, while layer of the adhesive solution was still undried, water drops with diameters of 500-800 μm were sprayed onto the surface of the layer of the adhesive solution in the proportion of 150 g/m², after which the specimen was dried, thereby obtaining the desired adhesive tape.

COMPARATIVE EXAMPLE 2

The adhesive solution obtained in the process of Example 2 was coated onto an air-permeable sheet in the proportion of 200 g/m² in the same manner as in Example 2. Then, while the layer of the adhesive solution was still undried, water drops with diameters of 500-800 μm were sprayed onto the surface of the layer of the adhesive solution in the proportion of 250 g/m², after which the specimen was dried. Residual water was observed on the surface of the adhesive layer even after the evaporation of the toluene. Finally, an air-permeable adhesive tape was obtained by evaporating the residual water.

EXAMPLE 4

An adhesive solution was obtained by polymerization, in ethyl acetate, of components consisting of 80 parts by weight of 2-ethylhexyl acrylate, 8 parts by weight of ethyl acrylate, 7 parts by weight of N-vinyl-2-pyrrolidone, 4.8 parts by weight of acrylic acid, and 0.2 parts by weight of 2-hydroxyethyl acrylate, and the solid content of the solution was adjusted to be 30% by weight by the addition of ethyl acetate.

Next, this adhesive solution was coated onto release paper in the proportion of 150 g/m², and while the layer of said adhesive solution was still undried water drops with diameters of 100-200 μm were sprayed onto the surface of the layer in the proportion of 75 g/m², after which the specimen was dried.

Next an air-permeable sheet was layered on the adhesive layer so obtained in order to transfer the said adhesive layer to the air-permeable sheet, thereby obtaining an air-permeable adhesive tape.

COMPARATIVE EXAMPLE 3

The adhesive solution obtained in the process of Example 3 was coated onto release paper in the proportion of 150 g/m², then, while layer of the adhesive solution was still undried, water drops with diameters 3-8 μm were sprayed onto the surface of the layer of the adhesive solution in the proportion of 75 g/m², after which the specimen was dried.

Next, an air-permeable sheet used in Example 1 was layered on the adhesive layer in order to transfer the said adhesive layer to the air-permeable sheet, thereby obtaining an air-permeable adhesive tape.

The results of measurements of physical properties of the air-permeable adhesive tapes obtained in the aforesaid Examples 1-4 and Comparative Examples 1-3 are shown in Table 1.

TABLE 1

| | Results from the observation by scanning electron microscope | | Air permeability (sec.) |
|---|---|---|---|
| | Diameter of pores (μm) | Number of pores/ 4 mm² | |
| Example 1 | 50-150 | 10-15 | 2.5 |
| Comparative Example 1 | 50-150 | 2-3 | 12.5 |
| Example 2 | 200-400 | 7-10 | 1.5 |
| Example 3 | 200-400 | 10-12 | 1.0 |
| Comparative Example 2 | 200-400 | 1-2 | 5.0 |
| Example 4 | 25-100 | 15-20 | 1.2 |
| Comparative Example 3 | No communicating pores | | 50000 or more |

EXAMPLE 5

An adhesive solution was obtained by polymerization, in toluene(interfacial tension between toluene and water is 36.25 dyn/cm at 20° C.), of components consisting of 80 parts by weight of 2-ethylhexyl acrylate, 8 parts by weight of ethyl acrylate, 7 parts by weight of N-vinyl-2-pyrrolidone, 4.8 parts by weight of acrylic acid, and 0.2 parts by weight of 2-hydroxyethyl acrylate, and the solid content of the solution was adjusted to be 40% by weight by the addition of toluene. The viscosity of the adhesive solution was 6000 cps.

Next, this adhesive solution was coated onto release paper in the proportion of 150 g/m², and while the layer of said adhesive solution was still undried, water drops with diameters of 100-200 μm were sprayed onto the surface of the layer in the proportion of 75 g/m², after which the specimen was dried, thus forming an adhesive layer on the release paper.

Next an air-permeable sheet was layered on the adhesive layer so obtained in order to transfer the said adhesive layer to the air-permeable sheet. The permeability of the adhesive tape so obtained was measured and found to be 0.8 sec.

EXAMPLE 6

An adhesive solution was obtained by polymerization, in cyclohexane (interfacial tension between cyclohexane and water is 50.59 dyn/cm at 20° C.), of components consisting of 80 parts by weight of 2-ethylhexyl acrylate, 8 parts by weight of ethyl acrylate, 7 parts by weight of N-vinyl-2-pyrrolidone, 4.8 parts by weight of acrylic acid, and 0.2 parts by weight of 2-hydroxyethyl acrylate, and the solid content of the solution was adjusted to be 40% by weight by the addition of ethyl acetate The weight ratio of cyclohexane and ethyl acetate contained in the adhesive solution was 75 : 25. The viscosity of the adhesive solution was 8000 cps.

Next, a layer of adhesive solution was formed by coating the aforesaid adhesive solution onto release paper in the proportion of 150 g/m$^2$, and while the layer of adhesive solution was still undried, water drops with diameters of 100-200 μm were sprayed onto the surface of the layer of the adhesive solution in the proportion of 75 g/m$^2$, after which the specimen was dried, thus forming an adhesive layer on the release paper.

Next, an air-permeable sheet was layered on the adhesive layer in order to transfer the adhesive layer to the air-permeable sheet. The permeability of the adhesive tape so obtained was measured and found to be 1.0 sec.

EXAMPLE 7

A resin solution was obtained by polymerization, in cyclohexane, of components consisting of 90 parts by weight of 2-ethylhexyl acrylate, 4 parts by weight of acrylic acid, 1 part by weight of 2-hydroxyethyl methacrylate, and 5 parts by weight of methyl methacrylate, and the solid content of the solution was adjusted to be 40% by weight by the addition of cyclohexane. The viscosity of the resin solution was 8000 cps. Then, 1 part by weight of COLONATE L (an isocyanate crosslinking agent manufactured by Nippon polyurethane industry Co., Ltd.) was added to the solution, thereby obtaining an adhesive solution.

Next, a layer of adhesive solution was formed by coating the aforesaid adhesive solution onto a release paper in the proportion of 100 g/m$^2$, and while the layer of adhesive solution was still undried, water drops containing 2% by weight of N,N'-hexamethylene-1,6-bis-(aziridinecarboxamide) (diameters of the water drops were 100-200 μm) were sprayed onto the surface of the layer of the adhesive solution in the proportion of 75 g/m$^2$, after which the specimen was dried, thus forming an adhesive layer on the release paper.

Next, an air-permeable sheet was layered on the adhesive layer in order to transfer the adhesive layer to the air-permeable sheet.

The permeability of the adhesive tape so obtained was measured and found to be 1.0 sec. The permeability of the tape measured after keeping it at 60° C. for 1 week was also 1.0 sec.

EXAMPLE 8

An air-permeable adhesive tape was obtained in the same manner as Example 7, except that pure water drops were applied in the proportion of 100 g/m$^2$ instead of the water drops containing N,N'-hexamethylene-1,6-bis(aziridinecarboxamide).

The permeability of the adhesive tape so obtained was measured and found to be 1.0 sec. The permeability of the tape measured after keeping it at 60° C. for 1 week was 10 sec.

EXAMPLE 9

An adhesive solution was obtained by polymerization, in cyclohexane, of components consisting of 88 parts by weight of 2-ethylhexyl acrylate, 1 part by weight of acrylic acid, 1 part by weight of 2-hydroxyethyl methacrylate, and 10 parts by weight of styrene macromer AS-6(manufactured by TOA GOSEI CHEMICAL INDUSTRY CO., LTD.; the macromer has a methacryloyl group at a terminal of the molecule and a number average molecular weight thereof is 6000), and the solid content of the solution was adjusted to be 40% by weight by the addition of cyclohexane. The viscosity of the adhesive solution was 7000 cps.

Next, a layer of adhesive solution was formed by coating the aforesaid adhesive solution onto release paper in the proportion of 100 g/m$^2$, and while the layer of adhesive solution was still undried, water drops with diameters of 100-200 μm were sprayed onto the surface of the layer of the adhesive solution in the proportion of 100 g/m$^2$. The specimen was dried at 110° C. for 5 minutes, thus, an adhesive layer was formed on the release paper.

Next, an air-permeable sheet was layered on the adhesive layer in order to transfer the adhesive layer to the air-permeable sheet.

The permeability of the adhesive tape so obtained was measured and found to be 1.0 sec.

EXAMPLE 10

An adhesive solution was obtained by polymerization, in toluene, of components consisting of 88 parts by weight of 2-ethylhexyl acrylate, 3 parts by weight of acrylic acid, 0.5 parts by weight of 2-hydroxyethyl methacrylate, 1.5 parts by weight of vinylpyrrolidone and 7 parts by weight of macromer AA-6(manufactured by TOA GOSEI CHEMICAL INDUSTRY CO., LTD.; the macromer is a polymethyl methacrylate having a number average molecular weight of 6000 and has a methacryloyl group at a terminal of the molecule), and the solid content of the solution was adjusted to be 40% by weight by the addition of toluene. The viscosity of the adhesive solution was 6000 cps.

Next, a layer of adhesive solution was formed by coating the aforesaid adhesive solution onto release paper in the proportion of 100 g/m$^2$, and while the layer of adhesive solution was still undried, water drops with diameters of 100-200 μm were sprayed onto the surface of the layer of the adhesive solution in the proportion of 100 g/m$^2$. The specimen was dried at 110° C. for 5 minutes, thus, an adhesive layer was formed on the release paper.

Next, an air-permeable sheet was layered on the adhesive layer in order to transfer the adhesive layer to the air-permeable sheet.

The permeability of the adhesive tape so obtained was measured and found to be 1.2 sec.

EXAMPLE 11

An adhesive solution was obtained by polymerization, in cyclohexane, of components consisting of 85 parts by weight of 2-ethylhexyl acrylate, 3 parts by weight of acrylic acid, 0.5 parts by weight of 2-hydroxyethyl methacrylate, 4.5 parts by weight of vinylpyrrolidone and 7 parts by weight of macromer AN-6(manufactured by TOA GOSEI CHEMICAL INDUSTRY CO., LTD.; the macromer is a copolymer of styrene and acrylonitrile having a number average molecular weight of 6000 and has a methacryloyl group at a terminal of the molecule), and the solid content of the solution was adjusted to be 30% by weight by the addition of cyclohexane. The viscosity of the adhesive solution was 6000 cps.

Next, a layer of adhesive solution was formed by coating the aforesaid adhesive solution onto release paper in the proportion of 150 g/m², and while the layer of adhesive solution was still undried, water drops with diameters of 100-200 μm were sprayed onto the surface of the layer of the adhesive solution in the proportion of 150 g/m². The specimen was dried at 110° C. for 5 minutes, thus, an adhesive layer was formed on the release paper.

Next, an air-permeable sheet was layered on the adhesive layer in order to transfer the adhesive layer to the air-permeable sheet.

The permeability of the adhesive tape so obtained was measured and found to be 0.5 sec.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A method for producing an air-permeable adhesive tape comprising a substrate and a porous adhesive layer formed on said substrate, comprising the steps of:
   forming a layer of a solution on a substrate, said solution containing an adhesive material in an organic solvent;
   applying water drops on said layer of said solution while said organic solvent remains in said layer, thereby allowing water drops to sink into said layer,
   the diameter of said water drops being in the range of 10 to 1000 μm, and the total amount of said water drops applied onto the surface of said layer being 5 to 200 g/m²;
   evaporating said organic solvent contained in said layer of the solution, thereby forming an adhesive layer that contains said water drops; and
   evaporating said water from said adhesive layer, thereby forming communicating pores extending from the external surface to the inner surface of said adhesive layer.

2. A method according to claim 1, wherein said substrate is an air-permeable sheet.

3. A method according to claim 1, wherein said substrate is a sheet with releasing properties, and said method further comprises the steps of, layering an air-permeable sheet on the surface of said adhesive layer with communicating pores, thereby transferring said adhesive layer onto said air-permeable sheet.

4. A method according to claim 1, wherein said adhesive material is a rubber-base or synthetic resin-base adhesive material.

5. A method according to claim 4, wherein said synthetic resin-base adhesive material comprises an acrylic adhesive which is a copolymer obtained from a macromer.

6. A method according to claim 5, wherein said macromer is a monomer of number average molecular weight 1,000 to 20,000 containing at least one vinyl group, and said monomer is at least one selected from the group consisting of polystyrene, polymethyl methacrylate, and polystyrene-acrylonitrile monomers.

7. A method according to claim 1, wherein the interfacial tension between said organic solvent and water is 20 dyn/cm or more at 20° C.

8. A method according to claim 1, wherein said water applied on the layer of the solution contains a crosslinking agent capable of crosslinking said adhesive material.

* * * * *